United States Patent [19]

Paparizos et al.

[11] Patent Number: 4,536,585
[45] Date of Patent: Aug. 20, 1985

[54] METHOD OF MAKING ACETALS BY CATALYTIC REACTION OF ALDEHYDES WITH HYDROXYALKANES

[75] Inventors: Christos Paparizos, Willowick; Robert S. Shout, Bedford Heights; Wilfrid G. Shaw, Lyndhurst, all of Ohio

[73] Assignee: The Standard Oil Company, Cleveland, Ohio

[21] Appl. No.: 557,775

[22] Filed: Dec. 5, 1983

[51] Int. Cl.$^3$ ............................................. C07D 317/00
[52] U.S. Cl. .................................. 549/453; 568/594; 568/600
[58] Field of Search ................. 568/600, 594; 549/453

[56] References Cited

U.S. PATENT DOCUMENTS

| | | | |
|---|---|---|---|
| 2,561,254 | 7/1951 | Whetstone et al. | 568/460 |
| 2,622,101 | 12/1952 | Paul et al. | 568/600 |
| 2,802,879 | 8/1957 | Guest et al. | 568/600 |
| 2,912,468 | 11/1959 | Copenhaver | 568/600 |

FOREIGN PATENT DOCUMENTS

| | | | |
|---|---|---|---|
| 669805 | 1/1939 | Fed. Rep. of Germany | 549/453 |
| 1023758 | 2/1958 | Fed. Rep. of Germany | 568/600 |

*Primary Examiner*—Ethel G. Love
*Attorney, Agent, or Firm*—Charles S. Lynch; John E. Miller, Jr.; Larry W. Evans

[57] ABSTRACT

It is disclosed that a Pd-Tl alloy catalyst is used in making acetals and acetalic ethers from alcohols and saturated or unsaturated aldehydes, and to make cyclic acetals and cyclic acetalic ethers when reacting with diols.

6 Claims, No Drawings

METHOD OF MAKING ACETALS BY CATALYTIC REACTION OF ALDEHYDES WITH HYDROXYALKANES

This invention relates to the production of acetals and acetalic ethers from aldehydes.

In the book, "Acrolein" by C. W. Smith, John Wiley Sons, Inc., New York, 1962, Chapter 7, it is disclosed that one might produce 3-ethoxypropionaldehyde diethyl acetal by the HCl catalyzed addition of ethyl alcohol to acrolein. Similarly, this book reports the reaction of lower alcohols with acrolein in the presence of an acid catalyst to make the alkoxypropionaldehyde dialkyl acetals. See pages 110 and 128-131. The acid catalysts must be separated from the desired product.

It is an object of the present invention to provide a catalytic process for making acetals and acetalic ethers, using a heterogenous solid catalyst easily separable from the reaction mixture.

It is a further object to provide a catalyst for such process, which catalyst is capable of providing high yields of acetals and acetalic ethers.

It is another object to provide a new ether-cyclic acetal,

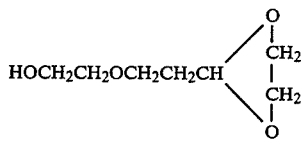

Other objects, as well as aspects, features, and advantages, of the invention will be apparent from the disclosure and claims.

These objects are attained according to the present invention in which there is provided a method for making acetals or acetalic ethers comprising reacting a $C_1$ to $C_{12}$, usually $C_1$ to $C_6$, saturated aldehyde or a $C_3$ to $C_{12}$, usually $C_3$ to $C_6$ unsaturated aldehyde with (1) a $C_1$ to $C_{12}$, usually $C_1$ to $C_6$, monohydroxyalkane, to produce an acetal, as follows:

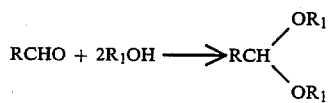

in the case of a saturated aldehyde, or to produce an acetalic ether, as follows:

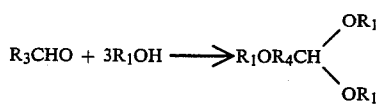

in the case of an unsaturated aldehyde, or with (2) a $C_2$ to $C_3$ dihydroxyalkane, to produce a closed ring acetal, as follows:

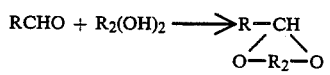

in the case of a saturated aldehyde, or to produce a closed ring acetalic ether, as follows:

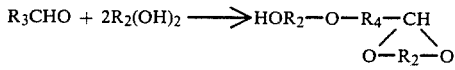

in the case of an unsaturated aldehyde, said reacting being effected by intimately contacting a mixture of the reactants with a particulate solid metallic catalyst comprising an alloy of palladium and thallium, wherein R is alkyl having 1-12 carbon atoms, usually -6 carbon atoms, $R_1$ is alkyl having 1-12 carbon atoms, usually 1-6 carbon atoms, $R_2$ is selected from $-CH_2CH_2-$, $-CH_2CH_2CH_2-$ and $-CH(CH_3)CH_2-$, $R_3$ is alkenyl having 2-12 carbon atoms, usually 2-6 carbon atoms, and $R_4$ is the hydrocarbon residue of the group resulting from the addition of a hydroxyl group in $R_1OH$ or $R_2(OH)_2$, across the double bond of $R_3$.

The reaction is usually effected in the temperature range of zero to 100° C., more usually 15°-60° C.

The invention broadly utilizes a Pd-Tl alloy, but an alloy in which the Pd to Tl ratio is 1:0.5 to 1:3 is usual, more often 1:0.5 to 1:2.5. It may be on a support such as silica but this is not necessary.

The molar ratio of the mono- or dihydroxyalkane to the aldehyde is usually at least 3:1, but it is more usually at least 10:1. There is no particular upper limit, but ratios of more than 50:1 are not needed and therefore entail needless expense.

In the process of the present invention it is easily possible to obtain high yields of the desired product, for instance, over 90 percent yields of 3-methoxypropionaldehyde dimethyl acetal, starting with acrolein and methanol. Moreover, since the catalyst is heterogeneous (a solid) it is very easy to separate from the final product in contrast to prior art homogenous catalysts.

The products of the invention are useful as additives to gasoline to promote solubilization of small amounts of water, as intermediates for surfactants, as a chain transfer agent, and as enhanced oil recovery agents. The acetals can also be reduced to the corresponding alcohols or ether-alcohols by reaction with sodium and ethyl alcohol; such alcohols also have the foregoing enumerated uses.

The following examples are merely illustrative and are not to be considered as limiting.

EXAMPLE 1 in a 200 cc beaker, 0.887 g of $PdCl_2$ and 2.66 of $TlNO_3$ were combined with 25 cc of concentrated (14N) $HNO_3$ and 50 cc of $H_2O$. Then the mixture was diluted up to 70 cc with Nalco 1034A (40 percent) silica sol and was stirred moderately with heating to about 60° C. The obtained solution was electrolyzed using a Pt wire anode, and a Cu (#14) wire as cathode by applying voltage (2-3 v) for 3 hours. The deposits which built up on the cathode was washed off with distilled water and collected periodically. The combined cathode deposits were washed using distilled water and dried in the oven over night at 110°-120° C. to yield a metallic alloy catalyst in powder form having an empirical formula $PdTl_{0.7}$. Most of the silica did not become part of the composition.

EXAMPLE 2

In a 200 cc beaker, 0.887 g of $PdCl_2$ and 2.28 g of $CdCl_2.2H_2O$ were combined with 10 cc of concentrated (11N) HCl and 65 cc of $H_2O$. Then the mixture was diluted up to 150 cc with Nalco 1034A (40 percent) silica sol and was stirred moderately with heating to about 60° C. The obtained solution was electrolyzed using a Pt wire anode, and a Cu (#14) wire as cathode by applying voltage (2–3 v) for 3 hours. The deposit which built up on the cathode was washed off with distilled water and collected periodically. The combined cathode deposits were washed using distilled water and dried in the oven over night at 110°–120° C. to yield a metallic alloy catalyst in powder form having the empirical formula $PdCd_{2.1}$. Most of the silica did not become part of the catalyst composition.

EXAMPLE 3

0.15 g of powdered $PdTl_{0.7}$, prepared as in Example 1, was placed in a 20 cc vial and the vial was sealed. The vial was then flushed with air for 15 minutes using inlet and outlet needles through the septum. Then with a syringe a mixture of 1.34 g methanol and 0.1 g acrolein was injected, and the reaction mixture stirred, by means of a small magnetic stirrer in the vial, for 16 hours at 50° C. The reaction mixture was analyzed in a Hewlett-Packard Model 5710A gas chromatograph filter with a flame ionization detector and a SP 1200 column. It was found that the yield of 3-methoxypropionaldehyde dimethyl acetal was over 93 percent and acrolein conversion was 100 percent.

EXAMPLE 4

0.15 g of powdered $PdTl_{0.7}$, prepared as in Example 1, was placed in a 20 cc vial and the vial was sealed. The vial was then flushed with oxygen for 15 minutes using inlet and outlet needles through the septum. Then with a syringe a mixture of 1.34 g methanol and 0.1 g acrolein was injected, and the reaction mixture stirred, by means of a small magnetic stirrer in the vial, for 16 hours at 50° C. The reaction mixture was analyzed in a Hewlett-Packard Model 5710A gas chromatograph filter with a flame ionization detector and a SP 1200 column. It was found that the yield of 3-methoxypropionaldehyde dimethyl acetal was 90 percent and acrolein conversion was 99 percent.

EXAMPLE 5

0.15 g of powdered $PdTl_{0.7}$, prepared as in Example 1, was placed in a 20 cc vial and the vial was sealed. The vial was then flushed with nitrogen for 15 minutes using inlet and outlet needles through the septum. Then with a syringe a mixture of 1.34 g methanol and 0.1 g acrolein was injected, and the reaction mixture stirred, by means of a small magnetic stirrer in the vial, for 16 hours at 50° C. The reaction mixture was analyzed in a Hewlett-Packard Model 5710A gas chromatograph filter with a flame ionization detector and a SP 1200 column. It was found that the yield of 3-methoxypropionaldehyde dimethyl acetal was 90 percent and acrolein conversion was 95 percent.

EXAMPLE 6

0.15 g of powdered $PdTl_{0.7}$, prepared as in Example 1, was placed in a 20 cc vial and the vial was sealed. The vial was then flushed with air for 15 minutes using inlet and outlet needles through the septum. Then with a syringe a mixture of 1.34 g methanol and 0.1 g acrolein was injected, and the reaction mixture stirred, by means of a small magnetic stirrer in the vial, for 16 hours at 21° C. The reaction mixture was analyzed in a Hewlett-Packard Model 5710A gas chromatograph filter with a flame ionization detector and a SP 1200 column. It was found that the yield of 3-methoxypropionaldehyde dimethyl acetal was 83 percent and acrolein conversion was 89 percent.

EXAMPLE 7

0.075 g of powdered $PdTl_{0.7}$, prepared as in Example 1, was placed in a 20 cc vial and the vial was sealed. The vial was then flushed with air for 15 minutes using inlet and outlet needles through the septum. Then with a syringe a mixture of 1.34 g methanol and 0.1 g acrolein was injected, and the reaction mixture stirred, by means of a small magnetic stirrer in the vial, for 16 hours at 50° C. The reaction mixture was analyzed in a Hewlett-Packard Model 5710A gas chromatograph filter with a flame ionization detector and a SP 1200 column. It was found that the yield of 3-methoxypropionaldehyde dimethyl acetal was 80 percent and acrolein conversion was 89.5 percent.

EXAMPLE 8

0.09 g of powdered $PdTl_{0.7}$, prepared as in Example 1, was placed in a 20 cc vial and the vial was sealed. The vial was then flushed with air for 15 minutes using inlet and outlet needles through the septum. Then with a syringe a mixture of 0.7 g methanol and 0.2 g acrolein was injected, and the reaction mixture stirred, by means of a small magnetic stirrer in the vial, for 16 hours at 50° C. The reaction mixture was analyzed in a Hewlett-Packard Model 5710A gas chromatograph filter with a flame ionization detector and a SP 1200 column. It was found that the yield of 3-methoxypropionaldehyde dimethyl acetal was 70 percent and acrolein conversion was 87.5 percent.

EXAMPLE 9

0.065 g of powdered Pd metal was placed in a 20 cc vial and the vial was sealed. The vial was then flushed with air for 15 minutes using inlet and outlet needles through the septum. Then with a syringe a mixture of 1.32 g methanol and 0.09 g acrolein was injected, and the reaction mixture stirred, by means of a small magnetic stirrer in the vial, for 16 hours at 50° C. The reaction mixture was analyzed in a Hewlett-Packard Model 5710A gas chromatograph filter with a flame ionization detector and a SP 1200 column. It was found that the yield of methyl acrylate was 26 percent but that no 3-methoxypropionaldehyde dimethyl acetal was formed. Acrolein conversion was 50 percent.

EXAMPLE 10

0.126 g of powdered Tl metal was placed in a 20 cc vial and the vial was sealed. The vial was then flushed with air for 15 minutes using inlet and outlet needles through the septum. Then with a syringe a mixture of 1.32 g methanol and 0.09 g acrolein was injected, and the reaction mixture stirred, by means of a small magnetic stirrer in the vial, for 16 hours at 50° C. The reaction mixture was analyzed in a Hewlett-Packard Model 5710A gas chromatograph filter with a flame ionization detector and a SP 1200 column. There was no conversion of the acrolein.

EXAMPLE 11

0.15 g of powdered PdCd$_{2.1}$, prepared as in Example 2, was placed in a 20 cc vial and the vial was sealed. The vial was then flushed with air for 15 minutes using inlet and outlet needles through the septum. Then with a syringe a mixture of 1.34 g methanol and 0.1 g acrolein was injected, and the reaction mixture stirred, by means of a small magnetic stirrer in the vial, for 16 hours at 50° C. The reaction mixture was analyzed in a Hewlett-Packard Model 5710A gas chromatograph filter with a flame ionization detector and a SP 1200 column. It was found that the yield of 3-methoxypropionaldehyde was over 93 percent and acrolein conversion was 100 percent, but no 3-methoxypropionaldehyde dimethyl acetal was formed.

EXAMPLE 12

0.04 g of powdered PdTl$_{0.7}$, prepared as in Example 1, was placed in a 20 cc vial and the vial was sealed. The vial was then flushed with air for 15 minutes using inlet and outlet needles through the septum. Then with a syringe a mixture of 0.87 g ethylene glycol and 0.03 g acrolein was injected, and the reaction mixture stirred, by means of a small magnetic stirrer in the vial, for 16 hours at 50° C. The reaction mixture was analyzed in a Hewlett-Packard Model 5710A gas chromatograph filter with a flame ionization detector and a SP 1200 column. It was found that major product was

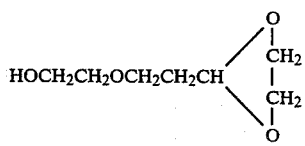

that the acrolein conversion was 90 percent.

EXAMPLE 13

0.04 g of powdered PdTl$_{0.7}$, prepared as in Example 1, was placed in a 20 cc vial and the vial was sealed. The vial was then flushed with air for 15 minutes using inlet and outlet needles through the septum. Then with a syringe a mixture of 0.583 g n-butanol and 0.017 g acrolein was injected, and the reaction mixture stirred, by means of a small magnetic stirrer in the vial, for 16 hours at 50° C. The reaction mixture was analyzed in a Hewlett-Packard Model 5710A gas chromatograph filter with a flame ionization detector and a SP 1200 column. It was found that the acrolein conversion was 86 percent and that the major product was 3-n-butoxypropionaldehyde di-n-butyl acetal.

EXAMPLE 14

0.04 g of powdered PdTl$_{0.7}$, prepared as in Example 1, was placed in a 20 cc vial and the vial was sealed. The vial was then flushed with air for 15 minutes using inlet and outlet needles through the septum. THen with a syringe a mixture of 0.643 g methanol and 0.057 g n-butyl aldehyde was injected, and the reaction mixture stirred, by means of a small magnetic stirrer in the vial, for 16 hours at 50° C. The reaction mixture was analyzed in a Hewlett-Packard Model 5710A gas chromatograph filter with a flame ionization detector and a SP 1200 column. It was found that the acrolein conversion was 87 percent and that the main product was n-butyraldehyde dimethyl acetal.

EXAMPLE 15

When Example 12 is repeated except that the diol is 1,3-propanol diol, the product is

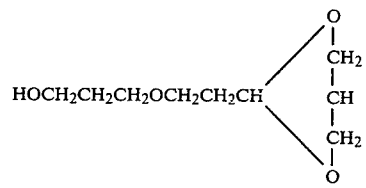

As will be evident to those skilled in the art various modifications of this invention can be made or followed in the light of the foregoing disclosure and discussion without departing from the spirit and scope of the disclosure or from the scope of the claims.

We claim:

1. A process which comprises reacting a C$_1$ to C$_{12}$ saturated aldehyde or a C$_3$ to C$_{12}$ unsaturated aldehyde with (1) a C$_1$ to C$_{12}$, monohydroxyalkane, to produce an acetal, as follows:

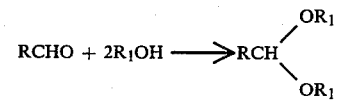

in the case of a saturated aldehyde, or to produce an acetalic ether, as follows:

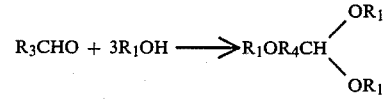

in the case of an unsaturated aldehyde, or with (2) a C$_2$ to C$_3$ dihydroxyalkane, to produce a closed ring acetal, as follows:

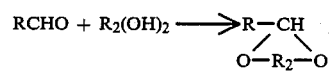

in the case of a saturated aldehyde, or to produce a closed ring acetalic ether, as follows:

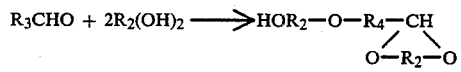

in the case of an unsaturated aldehyde, said reacting being effected by intimately contacting a mixture of the reactants with a particulate solid metallic catalyst comprising an alloy of palladium and thallium, wherein R is alkyl having 1-12 carbon atoms,
R$_1$ is alkyl having 1-12 carbon atoms,
R$_2$ is selected from —CH$_2$CH$_2$—, —CH$_2$CH$_2$CH$_2$— and —CH(CH$_3$)CH$_2$—,
R$_3$ is alkenyl having 2-12 carbon atoms, and $R_4$ is the hydrocarbon residue of the group resulting from the addition of a hydroxyl group in ROH or $R_2(OH)_2$, across the double bond of $R_3$.

2. A process which comprises reacting a $C_1$ to $C_6$ saturated aldehyde or a $C_3$ to $C_6$ unsaturated aldehyde with (1) a $C_1$ to $C_6$ monohydroxyalkane, to produce an acetal, as follows:

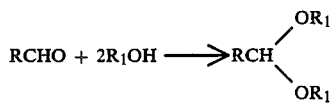

in the case of a saturated aldehyde, or to produce an acetalic ether, as follows:

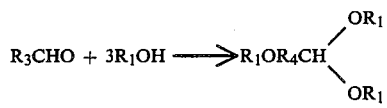

in the case of an unsaturated aldehyde or with (2) a $C_2$ to $C_3$ dihydroxyalkane, to produce a closed ring acetal, as follows:

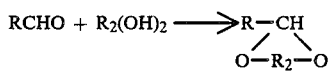

in the case of a saturated aldehyde, or to produce a closed ring acetalic ether, as follows:

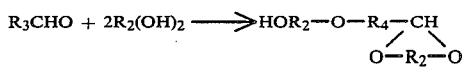

in the case of an unsaturated aldehyde, said reacting being effected by intimately contacting a mixture of the reactants with a particulate solid metalic catalyst comprising an alloy of palladium and thallium, wherein R is alkyl having 1-6 carbon atoms, $R_1$ is alkyl having 1-6 carbon atoms, $R_2$ is selected from $-CH_2CH_2-$, $-CH_2CH_2CH_2-$ and $-CH(CH_3)CH_2-$, $R_3$ is alkenyl having 2-6 carbon atoms, $R_4$ is the hydrocarbon residue of the group resulting from the addition of a hydroxyl group in $R_1OH$ or $R_2(OH)_2$, across the double bond of $R_3$.

3. A process according to claim 2 wherein methanol is reacted with acrolein to produce 3-methoxypropionaldehyde dimethyl acetal.

4. A process according to claim 2 wherein ethylene glycol and acrolein are reacted and the product is

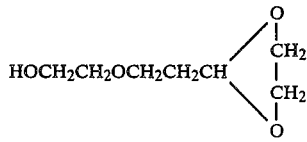

5. A process according to claim 2 wherein n-butanol and acrolein are reacted to produce 3-n-butoxypropionaldehyde di-n-butyl acetal.

6. A process according to claim 2 wherein methanol and n-butyl aldehyde are reacted to produce n-butyl aldehyde dimethyl acetal.

* * * * *